(12) United States Patent
Bernard et al.

(10) Patent No.: US 8,173,144 B2
(45) Date of Patent: *May 8, 2012

(54) ADMINISTRATION OF UREA COMPOUNDS FOR COMBATING SIGNS OF CUTANEOUS AGING

(75) Inventors: Dominique Bernard, Paris (FR); Lucie Simonetti, Vincennes (FR)

(73) Assignee: L'Oreal, Paris (FR)

(*) Notice: Subject to any disclaimer, the term of this patent is extended or adjusted under 35 U.S.C. 154(b) by 1171 days.

This patent is subject to a terminal disclaimer.

(21) Appl. No.: 11/260,139

(22) Filed: Oct. 28, 2005

(65) Prior Publication Data

US 2006/0127343 A1   Jun. 15, 2006

Related U.S. Application Data

(60) Provisional application No. 60/634,540, filed on Dec. 10, 2004.

(30) Foreign Application Priority Data

Nov. 4, 2004   (FR) ...................................... 04 11783

(51) Int. Cl.
*A61K 8/02* (2006.01)
(52) U.S. Cl. ..................................................... 424/401
(58) Field of Classification Search ........................ None
See application file for complete search history.

(56) References Cited

U.S. PATENT DOCUMENTS 6,100,277 A * 8/2000 Tucker et al. ................. 514/311
2001/0053347 A1   12/2001 Varani et al.
2005/0113269 A1 * 5/2005 Landa et al. .................. 510/130
2005/0186231 A1 * 8/2005 Zhang et al. .................. 424/401

FOREIGN PATENT DOCUMENTS

DE   27 03 185 A1   8/1978

OTHER PUBLICATIONS

Machine translation of DE 2703185 (pp. 1-6).*

(Continued)

*Primary Examiner* — Bethany Barham
(74) *Attorney, Agent, or Firm* — Buchanan Ingersoll & Rooney PC

(57) ABSTRACT

Signs of aging of the skin and/or mucous membranes are prevented and/or reduced, and the activity of the proteolytic enzymes of the stratum corneum are stimulated as well, by administering to an individual in need of such treatment, a cosmetic/pharmaceutical composition which comprises a thus effective amount of at least one hydroxylated urea compound having the following formula (I):

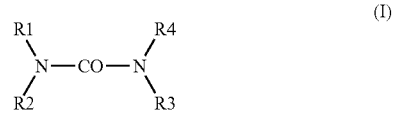

Figure 1:
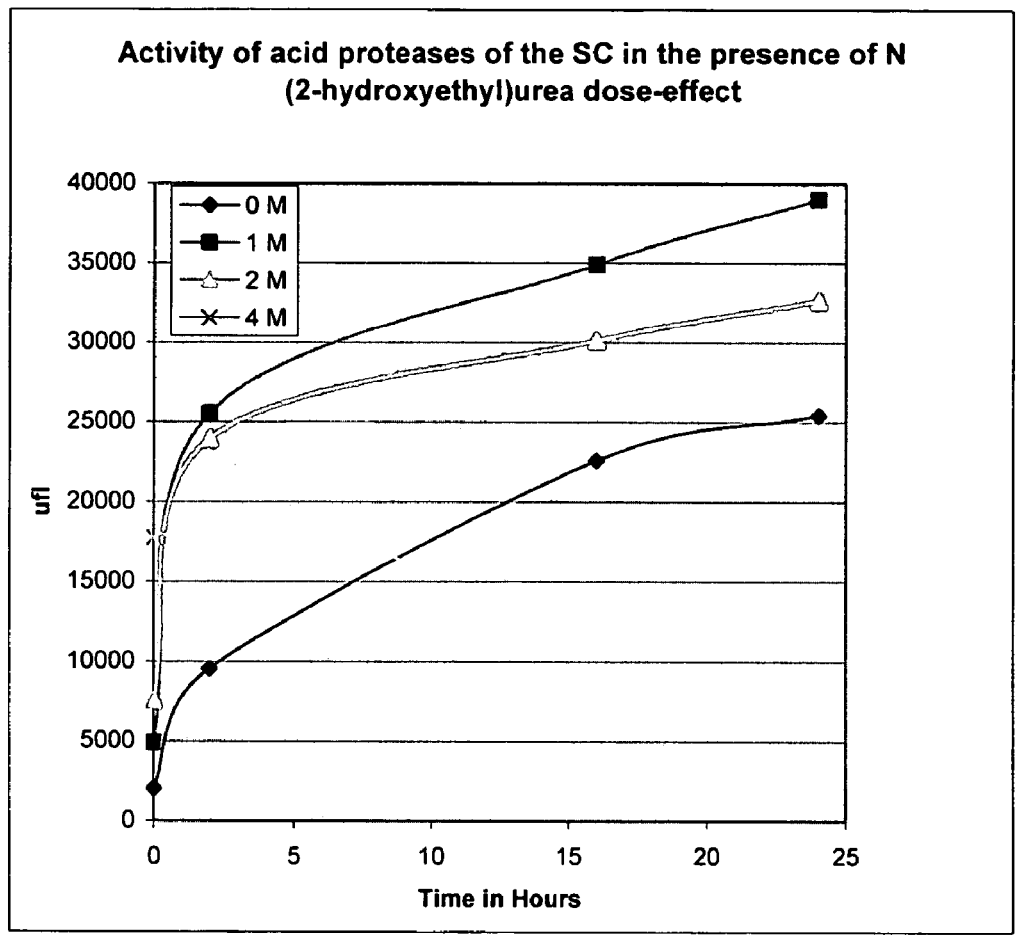
Figure 1:
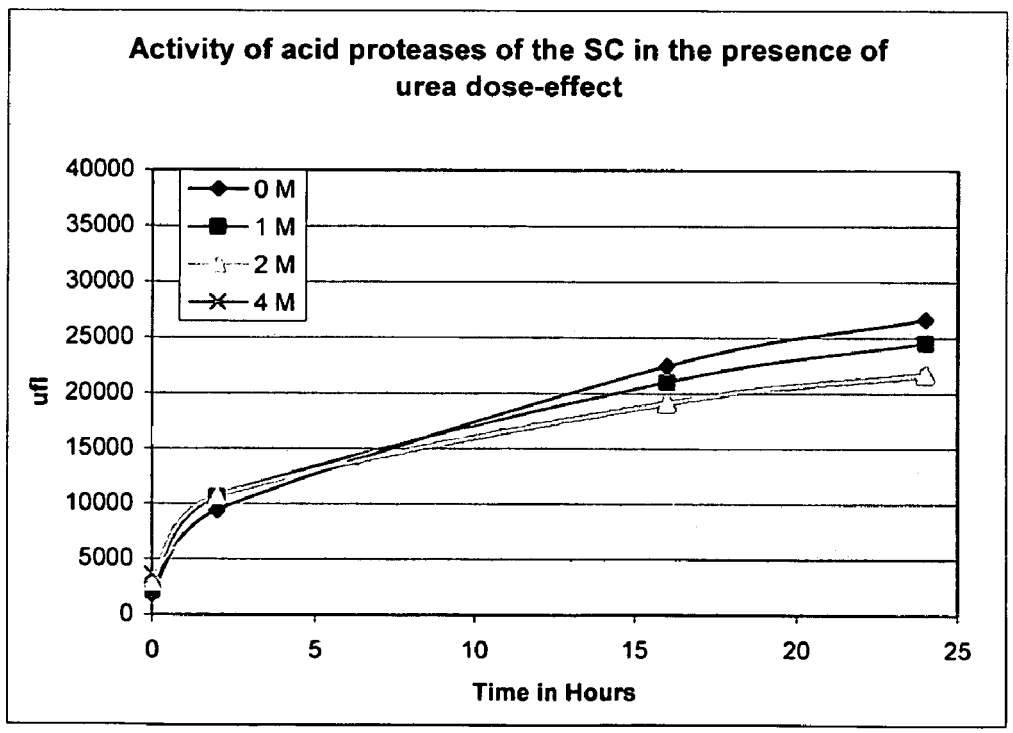

in which:
the radicals R1, R2, R3 and R4, which may be identical or different, are each a hydrogen atom, a $C_1$-$C_4$ alkyl radical or a $C_2$-$C_6$ hydroxyalkyl radical which can contain from 1 to 5 hydroxyl groups, wherein at least one of the R1 to R4 radicals represents a hydroxyalkyl radical, or salt, solvate or isomer thereof, formulated into a physiologically acceptable medium therefor.

17 Claims, 1 Drawing Sheet

OTHER PUBLICATIONS

Fuchs, Elaine; "Epidermal Differentiation: The Bare Essentials" The Journal of Cell Biology, vol. 111 (No. 6, Pt. 2) Dec. 1990; pp. 2807-2814.*

"Enhancing the deposition of benefit agents from a surfactant system onto hair and skin", IP Com Journal, IP Com Inc., Dec. 14, 2004, 6 pages, West Henrietta, NY, USA.

European Search Report Corresponding to EP 05 29 2332, Issued on Mar. 15, 2006, 1 Page.

French Search Report Corresponding to FR 04/11783, Issued on Jun. 27, 2005, 2 Pages.

Jensen et al., "Barrier Function, Epidermal Differentiation, and Human β-Defensin 2 Expression in *Tinea corporis*," *Journal of Investigative Dermatology* (2007), vol. 127, 1720-1727, The Society for Investigative Dermatology.

Van Der Vleuten et al., "Epidermal differentiation characteristics of the psoriatic plaque during treatment with calcipotriol," *Arch. DermataRes.*, (1996) 288:366-372, Springer-Verlag, The Netherlands.

Zeeuwen, "Epidermal differentiation: The role of proteases and their inhibitors," *Eur.J.Cell Biol.*, (2004):761-773, Elsevier, The Netherlands.

* cited by examiner

ADMINISTRATION OF UREA COMPOUNDS FOR COMBATING SIGNS OF CUTANEOUS AGING

CROSS-REFERENCE TO PRIORITY/PROVISIONAL APPLICATIONS

This application claims priority under 35 U.S.C. §119 of FR 04/11783, filed Nov. 4, 2004, and of provisional application Ser. No. 60/634,540, filed Dec. 10, 2004, each hereby expressly incorporated by reference and each assigned to the assignee hereof.

BACKGROUND OF THE INVENTION

1. Technical Field of the Invention

The present invention relates to the administration of at least one hydroxylated urea compound for combating signs of aging of the skin and mucous membranes.

2. Description of Background and/or Related and/or Prior Art

Women, and even men, currently have a tendency to wish to appear young for as long as possible and consequently wish to soften signs of aging of the skin, which are reflected in particular by wrinkles and fine lines, thinning of the epidermis, and/or skin with a flabby and withered appearance. On that subject, advertising and fashion promote products intended to retain a radiant and wrinkle-free skin for as long as possible, these being signs of a young skin, all the more so as the physical appearance affects the mind and/or the morale.

The skin is composed of two compartments, a surface compartment, the epidermis, and a deeper compartment, the dermis, which interact. The natural human epidermis is composed mainly of three types of cells, which are the keratinocytes, which form the vast majority, the melanocytes and the Langerhans cells. Each of these cell types contributes, via the specific functions thereof, to the essential role played by the skin in the body, in particular the role of protecting the body from external attacks, known as "barrier function"

The epidermis is conventionally divided into a basal layer of keratinocytes, which constitutes the germinal layer of the epidermis, a "prickle cell" layer, composed of several layers of polyhedral cells positioned on the germinal layers, one to three "granular" layers, composed of flattened cells comprising distinct cytoplasmic inclusions, keratohyalin granules, and finally the horny layer (or stratum corneum), composed of a combination of layers of keratinocytes at the terminal stage of their differentiation, known as corneocytes. Corneocytes are anucleate cells composed mainly of a fibrous material comprising cytokeratins which is surrounded by a horny envelope.

The dermis provides the epidermis with a firm support. It is also its nutrient element. It is mainly composed of fibroblasts and of an extracellular matrix composed predominantly of collagen, of elastin and of a substance referred to as ground substance. These components are synthesized by the fibroblasts. Leukocytes, mastocytes or even tissue macrophages are also found therein. Finally, blood vessels and nerve fibers pass through the dermis.

Cohesion between the epidermis and the dermis is provided by the dermal-epidermal junction.

New keratinocytes are continuously being produced in the epidermis in order to compensate for the continuous loss of epidermal cells at the horny layer.

However, during aging, epidermal proliferation and differentiation may be physiologically disrupted and a tendency for these two mechanisms to come into imbalance may be observed.

In addition, a deterioration in the proteasome system with age has been demonstrated (Friguet et al., 2002, *Scientific World Journal*). This may in part be related to an accumulation of oxidized proteins and thus to cell dysfunctioning (Dunlop, Rodgers et al., 2002; Szweda, Friguet et al., 2002). It will therefore be desirable to stimulate the activities in order to make up this deterioration.

The suggestion has been made that the stock of free amino acids in the stratum corneum decreases with the state of cutaneous dryness (Tanaka, Okada et al., 1998), which is accentuated in aged skin. These amino acids originate from the proteolysis of filaggrin. It is thus possible naturally to compensate for this deterioration in proteolysis of filaggrin by stimulating the protease activities for degradation of this protein.

Finally, the maturing of the HE (horny envelope), which can be detrimentally affected with age, is under the control of transglutaminase activities, themselves activated by proteolysis of a precursor; the activation of proteases involved in this processing would thus be of use.

Therefore, need continues to exist for novel means for combating one or more of these phenomena in order to prevent; delay or reduce the signs related to aging of the skin or mucous membranes.

SUMMARY OF THE INVENTION

Unexpectedly, it has now been found that urea derivatives exhibit an activity in stimulating the proteases of the skin.

Thus, the present invention features administration of at least one compound of following formula (I):

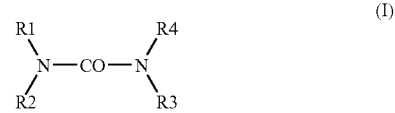

in which:

the radicals R1, R2, R3 and R4, which may be identical or different, are each a hydrogen atom, a $C_1$-$C_4$ alkyl radical or a $C_2$-$C_6$ hydroxyalkyl radical which can contain from 1 to 5 hydroxyl groups, wherein at least one of the R1 to R4 radicals represents a hydroxyalkyl radical, and their salts, their solvates and their isomers, formulated into a composition comprising a physiologically acceptable medium, as active agent for preventing and/or reducing signs of aging of the skin and/or mucous membranes.

The compounds of formula (I), their salts, their solvates and/or their isomers are useful, in particular, as agents for repairing or combating aging of the skin, whether photoinduced or chronological, or for reducing pigmentations and actinic keratoses, or any pathology associated with chronological or actinic aging.

DETAILED DESCRIPTION OF BEST MODE AND SPECIFIC/PREFERRED EMBODIMENTS OF THE INVENTION

For the compounds of formula (I):

preferably, R1 is a $C_2$-$C_6$ hydroxyalkyl radical and R2, R3 and R4 are each, independently of one another, a hydrogen atom or a $C_1$-$C_4$ alkyl radical;

preferably, R1 is a $C_2$-$C_6$ hydroxyalkyl radical comprising from 1 to 5 hydroxyl groups, in particular 1 hydroxyl group, and R2, R3 and R4 are each a hydrogen atom;

more preferably, R1 is a $C_2$-$C_4$ hydroxyalkyl radical containing 1 hydroxyl group and R2, R3 and R4 are each a hydrogen atom.

Mention may be made, among the alkyl radicals, of the methyl, ethyl, n-propyl, isopropyl, n-butyl, isobutyl and tert-butyl radicals.

Preference is given, among the hydroxyalkyl radicals, to those comprising a single hydroxyl group and in particular to the hydroxyethyl, hydroxypropyl, hydroxybutyl, hydroxypentyl and hydroxyhexyl radicals.

Mention may be made, among the salts, of salts of inorganic acids, such as sulfuric acid, hydrochloric acid, hydrobromic acid, hydriodic acid, phosphoric acid or boric acid. Mention may also be made of salts of organic acids which can comprise one or more carboxylic, sulfonic or phosphonic acid groups. They can be linear, branched or cyclic aliphatic acids or also aromatic acids. These acids can additionally comprise one or more heteroatoms selected from O and N, for example in the form of hydroxyl groups. Mention may in particular be made of propionic acid, acetic acid, terephthalic acid, citric acid and tartaric acid.

The term "solvate" means a stoichiometric mixture of the said compound of formula (I) with one or more molecules of water or of organic solvent, such a mixture resulting from the synthesis of the compound of formula (I).

Mention may be made, as preferred compounds of formula (I), of N-(2-hydroxyethyl)urea; N-(2-hydroxypropyl)urea; N-(3-hydroxypropyl)urea; N-(2,3-dihydroxypropyl)urea; N-(2,3,4,5,6-pentahydroxyhexyl)urea; N-methyl-N-(1,3,4,5,6-pentahydroxy-2-hexyl)urea; N-methyl-N'-(1-hydroxy-2-methyl-2-propyl)urea; N-(1-hydroxy-2-methyl-2-propyl)urea; N-(1,3-dihydroxy-2-propyl)urea; N-[tris(hydroxymethyl)methyl]urea; N-ethyl-N'-(2-hydroxyethyl)urea; N,N-bis(2-hydroxyethyl)urea; N,N'-bis(2-hydroxyethyl)urea; N,N-bis(2-hydroxypropyl)urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-(tert-butyl)-N'-(2-hydroxyethyl)-N'-(2-hydroxypropyl)urea; N-(1,3-dihydroxy-2-propyl)-N'-(2-hydroxyethyl)urea; N,N-bis(2-hydroxyethyl)-N',N'-dimethylurea; N,N,N',N'-tetrakis(2-hydroxyethyl)urea; N',N'-bis(2-hydroxyethyl)-N',N'-bis(2-hydroxypropyl)urea; and their mixtures.

Preferably, the compound of formula (I) is N-(2-hydroxyethyl)urea.

The compounds of formula (I) are known compounds and in particular are disclosed in DE-A-2,703,185. In addition, among these, N-(2-hydroxethyl)urea is commercially available from National Starch in the form of a 50% by weight mixture in water under the trademark Hydrovance®.

However, to the knowledge of the present inventors, these compounds had never been proposed for stimulating proteolytic activities and combating signs of aging.

The compounds of formula (I) can in particular be present in the compositions according to the invention in a content ranging from 0.1% to 50% by weight, with respect to the total weight of the composition, preferably ranging from 0.1% to 20% by weight and preferably ranging from 0.1% to 10% by weight.

A physiologically acceptable medium is, according to the invention, a cosmetically or pharmaceutically acceptable medium compatible with the skin, mucous membranes, nails and/or hair.

The compositions according to the invention can be topically applied to the nails, hair and more particularly skin and mucous membranes. The medium is preferably a cosmetically acceptable medium, that is to say one which exhibits a pleasant color, odor and feel and which does not cause unacceptable discomfort.

The compositions are preferably cosmetic compositions or products. The term "cosmetic product" means any substance or preparation suited to be brought into contact with the various surface parts of the human body (epidermis, hair, including body hair, nails, lips and external genital organs) or with the teeth and the oral mucous membranes, for the purpose, exclusively or principally, of cleaning them, of scenting them, of modifying the appearance thereof and/or of correcting body odors and/or of protecting them or of keeping them in good condition (amended cosmetics directive 76/768/EEC).

The compositions comprising a derivative of formula (I) according to the invention are particularly advantageous for acting on one or more epidermal mechanisms, such as the degradation of protein(s), the activation of enzyme(s) and/or the regulation of the phenomenon of epidermal differentiation/proliferation.

The present invention also features formulation of a compound of formula (I) into compositions useful to prevent and/or delay and/or reduce signs of aging of the skin and/or mucous membranes.

The compounds of formula (I) or the compositions comprising same will be of particular use in stimulating the activity of the proteolytic enzymes of the stratum corneum and thus in combating the disorders associated with a reduction in the activity of these enzymes related to age. These enzymes are selected in particular from among the group consisting of:

serine proteases, such as SCCE, SCTE, matriptase/MT-SP1, proprotein convertases or PEP1 (profilaggrin endoproteinase 1);

aspartic acid proteases, such as cathepsin D, cathepsin E or SASPase (Locuslink 151516);

cysteine proteases, such as cathepsin B, cathepsin H, cathepsin L, cathepsin L2, calpaines or caspase-14;

metalloproteases, such as MMP19 or carboxypeptidases.

Proteases have for a long time been characterized as non-specific degrading enzymes associated with the catabolism of proteins. However, it is becoming increasingly clear that proteolysis can represent a subtle mechanism for controlling certain biological processes occupying, for example, a specific location, the activation or inactivation of other enzymes, of cytokines, of hormones or of growth factors, the conversion of agonists to antagonists, and the like. Proteases thus directly modulate essential biological processes, such as DNA replication, the progression of the cell cycle, cell proliferation, differentiation and migration, morphogenesis or apoptosis. Proteases and their regulation are at key points in the regulation of the epidermal physiology. Various proteases belonging to virtually every category of protease known are associated with epidermal differentiation and are important elements in the regulation thereof.

According to the invention, the deterioration in the proteasome system can thus be combated by stimulating the activities of its proteases. It is possible to improve the degradation of the oxidized proteins and/or to improve the maturing of the horny envelope in aged skin and/or aged mucous membranes.

In particular, the compounds of formula (I) or the compositions comprising them will be of use in stimulating the activity of at least one acid protease of the stratum corneum. They will in particular be aspartic acid proteases, such as those disclosed in WO 04/007548.

The compounds of formula (I) are useful according to the invention for activating the enzymes for activation of transglutaminases and thus for promoting the cleavage of the inactive precursor to give the active form of the transglutaminases.

According to the invention, the urea derivatives of formula (I) are thus useful as agents for regulating epidermal differentiation, in particular in aged skin, and/or for promoting the degradation of filaggrin and inhibiting the reduction in the amount of free amino acids in the stratum corneum related to age. The invention also comprises the use of such compounds for the purpose of reducing the age-related accumulation of abnormal proteins.

Generally, any composition of the invention can be ingested, injected or topically applied to the skin (over any cutaneous region of the body) or to the mucous membranes (oral, jugal, gingival, genital, conjunctival, and the like).

Preferably, the compositions of the invention are topically applied onto the skin or mucous membranes.

Depending on the method of administration under consideration, the composition can be provided in any dosage form normally used.

For topical application to the skin, the composition can have the form in particular of aqueous or oily solutions or of dispersions of the lotion or serum type, of emulsions with a liquid or semi-liquid consistency of the milk type, obtained by dispersion of a fatty phase in an aqueous phase (O/W) or vice versa (W/O), or of suspensions or emulsions with a soft consistency of the aqueous or anhydrous gel or cream type, or else of microcapsules or microparticles, or of vesicular dispersions of ionic and/or nonionic type or of foams. These compositions are prepared according to the usual methods.

For injection, the composition can be provided in the form of aqueous or oily lotions or in the form of serums. For the eyes, the composition can be provided in the form of drops and, for ingestion, it can be provided in the form of capsules, granules, syrups or tablets.

The amounts of the various constituents of the compositions according to the invention are those conventionally used in the fields under consideration.

In the cosmetics field, these compositions constitute in particular creams for cleaning, protecting, treating or caring for the face, for the hands, for the feet, for the major anatomical folds or for the body (for example, day creams, night creams, make-up-removing creams, foundation creams or sun creams), liquid foundations, make-up-removing milks, protective or care body milks, sun milks, lotions, gels or foams for caring for the skin, such as cleansing lotions, sun lotions, artificial tanning lotions, bath compositions, deodorizing compositions comprising a bactericidal agent, after-shave gels or lotions, depilatory creams, compositions for countering insect stings or bites, pain-relieving compositions or compositions for treating certain skin diseases, such as eczema, rosacea, psoriasis, lichen and severe pruritus.

The compositions according to the invention can also be solid preparations constituting cleansing soaps or bars.

The compositions can also be packaged in the form of an aerosol composition also comprising a pressurized propellant.

A composition according to the invention can also be a composition for caring for the scalp, and in particular a shampoo, a hair-setting lotion, a treating lotion, a styling cream or gel, a dyeing composition (in particular an oxidation dyeing composition), optionally in the form of shampoo dyes, hair restructuring lotions, a perming composition (in particular a composition for the first step of a perming), a lotion or a gel for combating hair loss, an anti-parasitic shampoo, an anti-dandruff shampoo, and the like.

A composition can also be for oral use, for example, a toothpaste. In this case, the composition can comprise adjuvants and additives conventional for compositions for oral use and in particular surface-active agents, thickening agents, humectants, polishing agents, such as silica, various active ingredients, such as fluorides, in particular sodium fluoride, and optionally sweetening agents, such as sodium saccharinate.

When the composition is an emulsion, the proportion of the fatty phase can vary from approximately 5% to 80% by weight and preferably from approximately 5% to 50% by weight, with respect to the total weight of the composition. The oils, waxes, emulsifiers and coemulsifiers used in the composition in the emulsion form are selected from among those conventionally used in the cosmetics field. The emulsifier and coemulsifier are present in the composition in a proportion ranging from 0.3% to 30% by weight and preferably from 0.5% to 20% by weight, with respect to the total weight of the composition. In addition, the emulsion can comprise lipid vesicles.

When the composition is an oily solution or gel, the fatty phase can represent more than 90% of the total weight of the composition.

In known manner, the cosmetic composition can also comprise adjuvants conventional in the cosmetics field, such as hydrophilic or lipophilic gelling agents, hydrophilic or lipophilic additives, preservatives, antioxidants, solvents, fragrances, fillers, screening agents, odor absorbers and coloring materials. The amounts of these various adjuvants are those conventionally used in the cosmetics field and vary, for example, from approximately 0.01% to 10% of the total weight of the composition. These adjuvants, depending on their nature, can be introduced into the fatty phase, into the aqueous phase and/or into the lipid spherules.

Mention may be made, as oils or waxes which can be used in the invention, of mineral oils (liquid petrolatum), vegetable oils (liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. Fatty alcohols and fatty acids (stearic acid) can be added to these oils. Mention may be made, as emulsifiers which can be used in the invention, for example, of glyceryl stearate, polysorbate 60 and the PEG-6/PEG-32/glycol stearate mixture marketed under the name Tefose® 63 by Gattefossé.

Mention may be made, as solvents which can be used in the invention, of lower alcohols, in particular ethanol and isopropanol, and propylene glycol.

Mention may be made, as hydrophilic gelling agents which can be used in the invention, of carboxyvinyl polymers (Carbomer®), acrylic copolymers, such as acrylate/alkylacrylate copolymers, polyacrylamides, polysaccharides, such as hydroxypropylcellulose, natural gums and clays, and mention may be made, as lipophilic gelling agents, of modified clays, such as bentones, metal salts of fatty acids, such as aluminum stearates, hydrophobic silica, ethylcellulose and polyethylene.

According to one of the embodiments of the invention, at least one compound of formula (I) or one of its derivatives as described above, as agent for combating signs of aging of the skin and/or mucous membranes, is administered in combination with at least one agent which stimulates the synthesis of certain dermal and/or epidermal macromolecules, and/or at least one agent which inhibits their degradation, and/or at least one agent which stimulates the proliferation of fibroblasts and/or keratinocytes and/or at least one agent which stimulates the differentiation of keratinocytes.

This is because it may be advantageous to combine the activity of stimulating the activity of proteases of the stratum corneum by the compounds of formula (I) according to the invention with inhibition of certain proteolytic enzymes, in particular active in the dermis, which can have a harmful activity for the maintenance of the properties of the skin. It is also advantageous to reinforce the activity with regard to differentiation and the barrier function of the agents according to the invention with agents which modulate the differentiation and/or the proliferation of the cells of the skin.

Mention may be made, among active principles which stimulate the macromolecules of the dermis or prevent their degradation, of those which act:

either on the synthesis of collagen, such as extracts of Centella asiatica; asiaticosides and derivatives; ascorbic acid or vitamin C and its derivatives, such as ascorbyl glucoside (marketed by Hayashibara); synthetic peptides, such as iamine, the palmitoyl of glycine-histidine-lysine tripeptide, marketed under the name "Biopeptide CL" by Sederma; peptides extracted from plants, such as the soybean hydrolysate marketed by Coletica under the trademark Phytokine®; extracts of soya fibers, such as that marketed under the name "Raffermine" by Silab; plant hormones, such as auxins and lignans; the palmitoyl of lysine-threonine-threonine-lysine-serine pentapeptide marketed in particular under the name "Matrixyl" by Sederma; dimethylaminoethanol; extracts of Bupleurum chinensis rhizome, such as those marketed under the names "Pleurimincyl" or "Lipocare" by Sederma; acylated with a hydrolysates of wheat protein, in particular acylated with a palmitoyl group, such as that marketed under the name "Lipacid PVB" by Seppic; creatine; coenzyme Q10; retinol; dipalmitoyl hydroxyproline, in particular marketed by Seppic under the name "Sepilift DPHP", or extracts of red clover (Trifolium pretense) comprising isoflavones;

or on the synthesis of elastin, such as the extract of Saccharomyces cerivisiae marketed by LSN under the trademark Cytovitin®; and the extract of the alga Macrocystis pyrifera marketed by Secma under the trademark Kelpadelie®;

or on the synthesis of glycosaminoglycans, such as the product of fermentation of milk by Lactobacillus vulgaris marketed by Brooks under the trademark Biomin yogourth®; the extract of the brown alga Padina pavonica marketed by Alban Müller under the trademark HSP3®; and the extract of Saccharomyces cerevisiae available in particular from Silab under the trademark Firmalift® or from LSN under the trademark Cytovitin®;

or on the synthesis of fibronectin, such as the extract of Salina zooplankton marketed by Seporga under the trademark GP4G®; the yeast extract available in particular from Alban Müller under the trademark Drieline®; and the palmitoyl pentapeptide marketed by Sederma under the trademark Matrixil®;

or on the synthesis of compounds present at the dermal-epidermal junction (such as collagen VII and/or collagen IV) and/or laminin, such as dipalmitoyl hydroxyproline, marketed in particular by Seppic under the name "Seppilift DPHP", or phytosterol sulfate, such as that marketed by Vincience under the name "Phytocohesine";

or on the inhibition of metalloproteinases (matrix metalloproteinases or MMPs), such as more particularly MMP 1, 2, 3 or 9. Mention may be made of retinoids and derivatives, oligopeptides and lipopeptides, lipoamino acids, the malt extract marketed by Coletica under the trademark Collalift®; extracts of blueberry or of rosemary; lycopene; isoflavones, their derivatives or the plant extracts comprising them, in particular extracts of soybean (marketed, for example, by Ichimaru Pharcos under the trademark Flavosterone SB®), of red clover (marketed, for example, by Sederma under the trademark "Sterocare®"), of flax, of kakkon or of sage; extracts of Curcuma longa; or Siegesbeckia extracts (marketed, for example, by Sederma);

or on the inhibition of serine proteases, such as leukocyte elastase or cathepsin G. Mention may be made of the peptide extract of leguminous plant (Pisum sativum) seeds marketed by LSN under the trademark Parelastyl®; heparinoids; and pseudodipeptides, such as {2-[acetyl(3-(trifluoromethyl)phenyl)amino]-3-methylbutyrylamino}acetic acid.

Other protease-inhibiting agents which can be used in combination according to the invention are plasminogen activation inhibitors, such as, for example, tranexamic acid.

Mention may in particular be made, among the active principles which stimulate epidermal macromolecules, such as filaggrin and keratins, of the lupin extract marketed by Silab under the trademark Structurine®; the extract of beech Fagus sylvatica buds marketed by Gattefossé under the trademark Gatuline®; and the extract of Salina zooplankton marketed by Seporga under the trademark GP4G®.

The agents which stimulate the proliferation of fibroblasts which can be used in the composition according to the invention can, for example, be selected from among plant proteins or polypeptides, extracts, in particular of soybean (for example, a soybean extract marketed by LSN under the name Eleseryl SH-VEG 8® or marketed by Silab under the trademark Raffermine®); and plant hormones, such as gibberellins and cytokinins.

The agents which stimulate the proliferation of keratinocytes which can be formulated into the compositions according to the invention comprise in particular retinoids, such as retinol and its esters, including retinyl palmitate; adenosine; phloroglucinol; the extracts of walnut meal marketed by Gattefossé; and the extracts of Solanum tuberosum marketed by Sederma.

The agents which stimulate the differentiation of keratinocytes comprise, for example, inorganic materials, such as calcium; a lupin peptide extract, such as that marketed by Silab under the trademark Structurine®; sodium β-sitosteryl sulfate, such as that marketed by Seporga under the trademark Phytocohesine®; a water-soluble maize extract, such as that marketed by Solabia under the trademark Phytovityl®; a peptide extract of Voandzeia subterranea, such as that marketed by Laboratoires Sérobiologiques under the trademark Filladyn LS 9397®; and lignans, such as secoisolariciresinol.

The compositions according to the invention including one or more of the above compounds are particularly well suited for the prevention or treatment of cutaneous signs of aging, in particular of loss of firmness and/or of elasticity of the skin.

This invention also features a cosmetic treatment regime or regimen for reducing and/or delaying signs of aging of the skin and/or mucous membranes, in which at least one compound of formula (I) or one of its salts, solvates or isomers, or a composition comprising same as defined above, is topically applied to the regions of the skin or mucous membranes concerned. Application can be daily or twice daily and can be repeated for several days, several weeks and/or several months.

In order to further illustrate the present invention and the advantages thereof, the following specific example is given, reference being made to the single appended FIGURE, in which is represented the quantitative determination of the protease activity for the proteins of the SC (results expressed as unit of fluorescence), it also being understood that same is intended only as illustrative and in nowise limitative.

Example

Activation of Acid Proteases

The property of activating certain acid proteases of the SC (stratum corneum) is evaluated. This activity is measured by virtue of a quantitative determination by fluorimetry using the Enzchek kit (Molecular Probes). This protocol uses a Bodipy FL casein substrate which releases fluorescence when it is hydrolyzed. The fluorescence released is directly proportional to the protease activity. It is read directly in a 96-well plate with a spectrofluorimeter at 750 V at 485 nm in excitation and 535 nm in emission.

The results obtained with N-(2-hydroxyethyl)urea (compound according to the invention) are compared with those of urea.

Procedure

The molecules are prepared at 0, 1, 2 and 4M in a 0.1M; pH 5.0; acetate buffer.

An enzyme extract is prepared from acetone powders.

2 ml of PBS buffer+0.1% of Triton X100 are brought into contact for 1 h in crushed ice with 200 mg of stratum corneum acetone powders. The mixture is subsequently ground in a Potter homogenizer and then centrifuged at 15 000 g for 10 min at 4° C. The supernatant is collected. The Enzchek substrate, diluted to 1/200, is incorporated in each solution comprising the molecules. The assays are repeated three times.

The reaction mixture is prepared directly in a white plate.

10 μl of enzyme extract are added to 200 μl of solution comprising the substrate at 0, 1, 2 or 4M. The readings are carried out at t0, t 2h, t 16h and t 24h.

The results are represented in the appended FIGURE.

Urea at 1 and 2M has a slightly activating effect on the acid proteases up to two hours after the beginning of the incubation.

On the other hand, for N-(2-hydroxethyl)urea, a significant increase in the activity for the concentrations of 1 and 2M is recorded with respect to the control. This increase is lasting over time. At 4M, a marked decrease in the activity is observed, whatever the time studied.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for regulating epidermal differentiation, and/or inhibiting the reduction in the amount of free amino acids in the stratum corneum related to age, and/or reducing the age-related accumulation of abnormal proteins, the regime or regimen comprising:

administering to an individual in need of such treatment, a cosmetic/pharmaceutical composition which comprises a thus effective amount of at least one hydroxylated urea compound having the following formula (I):

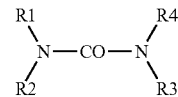

in which:

the radicals R1, R2, R3 and R4, which may be identical or different, are each a hydrogen atom, a $C_1$-$C_4$ alkyl radical or a $C_2$-$C_6$ hydroxyalkyl radical which can contain from 1 to 5 hydroxyl groups, wherein at least one of the R1 to R4 radicals represents a hydroxyalkyl radical, or salt, solvate or isomer thereof, formulated into a physiologically acceptable medium therefor; and regulating epidermal differentiation, and/or inhibiting the reduction in the amount of free amino acids in the stratum corneum related to age, and/or reducing the age-related accumulation of abnormal proteins; and said effective amount of the compound of formula (I) is an amount equivalent to that observed in an in vitro measurement of protease activity for the same compound at concentrations of from 1M to 4M.

2. The regime or regimen as defined by claim 1, for regulating epidermal differentiation.

3. The regime or regimen as defined by claim 1, for inhibiting the reduction in the amount of free amino acids in the stratum corneum related to age.

4. The regime or regimen as defined by claim 1, for reducing the age-related accumulation of abnormal proteins.

5. The regime or regimen as defined by claim 1, said cosmetic/pharmaceutical composition further comprising at least one active agent which reduces and/or inhibits the activity of harmful proteases.

6. The regime or regimen as defined by claim 5, said cosmetic/pharmaceutical composition further comprising at least one active agent which inhibits MMPs and/or at least one active agent which inhibits the activation of plasminogen.

7. The regime or regimen as defined by claim 1, wherein formula (I), R1 is a $C_2$-$C_6$ hydroxyalkyl radical and R2, R3 and R4, which may be identical or different, are each a hydrogen atom or a $C_1$-$C_4$ alkyl radical.

8. The regime or regimen as defined by claim 1, wherein formula (I), R1 is a $C_2$-$C_6$ hydroxyalkyl radical having from 1 to 5 hydroxyl groups and R2, R3 and R4 are each a hydrogen atom.

9. The regime or regimen as defined by claim 1, wherein formula (I), R1 is a $C_2$-$C_6$ hydroxyalkyl radical having 1 hydroxyl group.

10. The regime or regimen as defined by claim 1, wherein formula (1), R1 is a $C_2$-$C_4$ hydroxyalkyl radical having 1 hydroxyl group and R2, R3 and R4 are each a hydrogen atom.

11. The regime or regimen as defined by claim 1, said at least one hydroxylated urea compound of formula (1) being selected from the group consisting of N-(2-hydroxyethyl) urea; N-(2-hydroxypropyl)urea; N-(3-hydroxypropyl)urea; N-(2,3-dihydroxypropyl)urea; N-(2,3,4,5,6-penta-hydroxy-hexyl)urea; N-methyl-N-(1,3,4,5,6-pentahydroxy-2-hexyl) urea; N-methyl-N'-(1-hydroxy-2-methyl-2-propyl)urea; N-(1-hydroxy-2-methyl-2-propyl)urea; N-(1,3-dihydroxy-2-propyl)urea; N4-tris(hydroxy-methyl)methyl]urea; N-ethyl-N'-(2-hydroxyethyl)urea; N,N-bis(2-hydroxyethyl)urea; N,N'-bis(2-hydroxyethyl)urea, N,N-bis(2-hydroxypropyl) urea; N,N'-bis(2-hydroxypropyl)urea; N,N-bis(2-hydroxyethyl)-N'-propylurea; N,N-bis(2-hydroxypropyl)-N'-(2-hydroxyethyl)urea; N-(tert-butyl)-N'-(2-hydroxyethyl)-N'-(2- hydroxypropyl)urea; N-(1,3-dihydroxy-2-propy1)-N'-(2-hydroxyethyl)urea; N,N-bis(2-hydroxyethyl)-N',N'-dimethylurea; N,N,N',N'-tetrakis(2-hydroxyethyl)urea; N',N'-bis(2-hydroxyethyl)-N',N'-bis(2-hydroxypropyl)urea; and mixtures thereof.

12. The regime or regimen as defined by claim 11, said at least one hydroxylated urea compound of formula (1) being N-(2-hydroxyethyl)urea.

13. The regime or regimen as defined by claim 1, comprising topically applying said cosmetic/pharmaceutical composition onto the skin and/or mucous membranes of said individual.

14. The regime or regimen as defined by claim 1, said cosmetic/pharmaceutical composition being formulated for administration by injection.

15. The regime or regimen as defined by claim 1, said cosmetic/pharmaceutical composition being formulated for administration by oral ingestion.

16. The regime or regimen as defined by claim 1, further comprising: reducing pigmentations and actinic keratoses.

17. The regime or regimen as defined by claim 1, further comprising: treating loss of firmness and/or elasticity of the skin.

* * * * *